(12) United States Patent
Matsumoto et al.

(10) Patent No.: US 6,193,699 B1
(45) Date of Patent: Feb. 27, 2001

(54) MEDICAL TUBE

(75) Inventors: Takashi Matsumoto; Hajime Tsujikawa, both of Osaka; Shunichi Hayashi; Satoru Kondo, both of Nagoya; Atsushi Utsumi, Itami; Tamotsu Kaide, Amagasaki, all of (JP)

(73) Assignees: Nissho Corporation, Osaka; Mitsubishi Jukogyo Kabushiki Kaisha, Tokyo; Mitsubishi Cable Industries, Ltd., Amagasaki; Mitsubishi Corporation, Tokyo, all of (JP)

( * ) Notice: Subject to any disclaimer, the term of this patent is extended or adjusted under 35 U.S.C. 154(b) by 0 days.

(21) Appl. No.: 08/229,115

(22) Filed: Apr. 18, 1994

Related U.S. Application Data

(63) Continuation of application No. 07/845,598, filed on Mar. 4, 1992, now abandoned.

(30) Foreign Application Priority Data

Mar. 8, 1991 (JP) .................................................... 3-069344

(51) Int. Cl.$^7$ ............................. A61M 25/00; A61M 5/32
(52) U.S. Cl. ............................................ 604/265; 604/523
(58) Field of Search ..................................... 604/264, 280, 604/281, 282, 265, 272, 523, 524, 530, 531; 128/658; 524/44, 83

(56) References Cited

U.S. PATENT DOCUMENTS

| | | | | |
|---|---|---|---|---|
| 4,371,686 | * | 2/1983 | Yamamoto et al. | 528/76 |
| 4,424,305 | * | 1/1984 | Gould et al. | 525/127 |
| 4,722,344 | * | 2/1988 | Cambron et al. | 604/280 |
| 4,780,512 | * | 10/1988 | Gould et al. | 525/454 |
| 4,789,720 | * | 12/1988 | Teffenhart | 528/76 |
| 4,810,582 | * | 3/1989 | Gould et al. | 128/849 |
| 4,994,047 | * | 2/1991 | Walker et al. | 604/280 |
| 4,999,210 | * | 3/1991 | Solomon et al. | 604/266 |
| 5,102,401 | * | 4/1992 | Lambert et al. | 604/264 |
| 5,159,050 | * | 10/1992 | Onwumere | 528/67 |

FOREIGN PATENT DOCUMENTS

| | | |
|---|---|---|
| 0367014 | 5/1990 | (EP) . |
| 3-49767 | 3/1991 | (JP) . |
| 3-60672 | 3/1991 | (JP) . |
| 90/11793 | 10/1990 | (WO) . |

* cited by examiner

*Primary Examiner*—Ronald K. Stright, Jr.
(74) *Attorney, Agent, or Firm*—Varndell & Varndell, PLLC

(57) ABSTRACT

A medical tube made of an organic polymer having a mechanical loss tangent of at least 0.5 at body temperature and a modulus of transverse elasticity of 1–1000 MPa at body temperature. The medical tube of the present invention can be easily inserted into the body, and gives less pain and less feeling of physical disorder during indwelling in the body or removal from the body.

1 Claim, 1 Drawing Sheet

MEDICAL TUBE

This application is a continuation application of Ser. No. 07/845,598 filed Mar. 4, 1992 now abandoned.

BACKGROUND OF THE INVENTION

The present invention relates to a medical tube for animals, particularly humans. More specifically, the present invention relates to a catheter, an intravenous cannula (hereinafter briefly referred to as cannula), a bougie, and other medical tubes used for the examination, observation, prevention and treatment of diseases, such as conduit tubes for introducing liquids into and out of the body, tubes used for vasodilation and removal of thrombus and embolus, artificial blood vessels, artificial tracheae, and so on.

Medical tubes are, for example, inserted into blood vessels, particularly coronary artery, trachea, oviduct, urinary duct, various organs, and so on for the purpose of injection of liquids, aspiration, or patency of ducts. The catheters recently proposed are equipped with many functions besides the ordinary functions mentioned above, such as an illumination fiber and an image guide for endoscope, and some are even equipped with a flash hole. U.S. Pat. No. 4,846,812 proposes a cannula made of a shape memory polymer.

There are many people who become unpleasant or in some cases, suffer from pain upon insertion of a medical tube into the body, during indwelling thereof in the body and/or upon removal thereof from the body (such unpleasantness and condition of the body are hereinafter generally referred to as "feeling of physical disorder" in the present invention). However, such feeling of physical disorder is considered to be of little significance in conventional medical tubes, and naturally, no measures are taken to avoid the feeling of physical disorder. The cannula disclosed in the above-mentioned US patent ignores this aspect. While said cannula reduces swelling with body fluids by employing a two-layer structure with the inner layer composed of a non-hydrophilic resin, since its constituent material is highly hydrophilic, the cannula cannot prevent swelling on being contacted with blood, etc. after insertion into the body, and has a serious defect in that it increases the feeling of physical disorder. Combined with the restriction on the body which is caused by indwelling of a medical tube in the body, such feeling of physical disorder can give a physical, as well as psychological pain.

In the meantime, the enteral Diet catheter (ED catheter) has been drawing attention in recent years. The ED catheter is indwelled in duodenum via mouth or nose, throat, esophagus, and stomach for the administration of component nutrients, enteral nutrients, and liquid diet. At present, ED catheters made of EVA (ethylene-vinyl acetate copolymer) or silicone are being used. Those made of EVA are stiff and can be inserted easily, but give a strong pain and a strong feeling of physical disorder. On the other hand, those made of silicone are too soft to be easily inserted. Therefore, an ED catheter which can be easily inserted and gives less pain and less feeling of physical disorder during insertion and indwelling is desired.

SUMMARY OF THE INVENTION

An object of the present invention is to provide a medical tube which can be easily inserted into the body and gives less pain and less feeling of physical disorder during indwelling in the body and removal therefrom.

The present inventors have made intensive studies for the purpose of achieving the above object, and found that a medical tube made of an organic polymer having a specific mechanical loss tangent and a specific modulus of transverse elasticity to be mentioned later satisfies the requirements of the object, and that the feeling of physical disorder can be remarkably reduced by selecting water absorption of the tube to be inserted into the body from a specific range.

That is, the medical tube of the present invention is made of an organic polymer having a mechanical loss tangent of at least 0.5 at body temperature, and a modulus of transverse elasticity of 1–1000 MPa at body temperature, and in a preferred embodiment, the water absorption of said organic polymer at body temperature is 5 wt % or less.

DETAILED DESCRIPTION OF THE INVENTION

Figure 1:
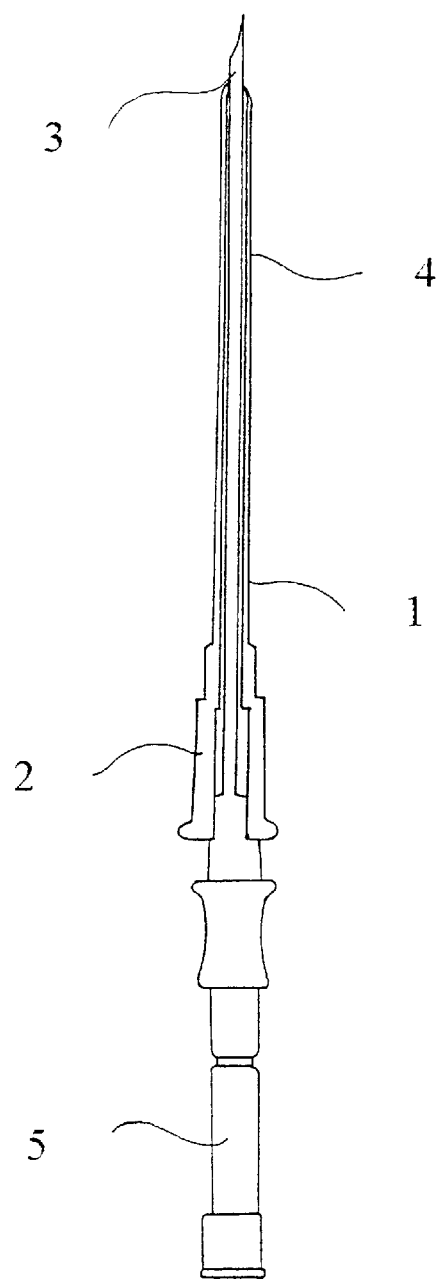
FIG. 1 is a cross section of the cannula used in Experiments.

The medical tube of the present invention includes all medical instruments in the form of a tube, such as catheter, cannula, irrigator, bougie, and the like, which can be inserted into the body of animals including human, for the purpose of examination, observation, diagnosis, treatment, prevention and/or other purposes. That is, the tube of the present invention is made of a particular organic polymer, and includes various modifications depending on the object of use, functions, and application range such as circulatory system, aspiratory system, digestive system, urinary system, genital system, and so on, which are exemplified by those having functions such as liquid injection and discharge function, body temperature measuring function, blood pressure measurement and blood examination functions, chemical analysis function, endoscopic function, and those equipped with a laser fiber or a balloon.

Examples of the medical tube are intravenous catheter, cardiac catheter, angiography catheter, vasodilation catheter, thrombus removing catheter, cholangiocatheter, bronchus tube, stomach tube, peridural catheter, esophagus bougie, middle cardiac vein catheter, drainage tube, pancreatic duct tube, cervical canal indwelling catheter, endoscope catheter, urine discharge catheter, nasotracheal oxygen catheter, suction catheter, trocar catheter, ED catheter, solution infusion tube, and so on.

The medical tube of the present invention is applicable to mammals including humans (e.g. cow, rabbit, horse, sheep, monkey, dog, cat, etc.). Accordingly, the body temperature in the present invention means that of these animals, which varies depending on the animal species.

The organic polymer formulating the medical tube of the present invention has a mechanical loss tangent (tan $\delta_T$) of at least 0.5 at body temperature (T° C.), preferably at least 1.0, and more preferably at least 2.0. Where tan $\delta_T$ is less than 0.5, the tube is so stiff as to thrust against the surrounding tissue while inserted in the body, and gives a feeling of physical disorder. With this tan $\delta_T$, the tube may give a pain when the muscle around the tube moves.

The medical tube of the present invention has a modulus of transverse elasticity ($G_T$) of 1–1000 MPa at body temperature, preferably 10–500 MPa, and more preferably 20–100 MPa. With a $G_T$ over 1000 MPa, said medical tube always thrusts against the surrounding tissue due to the exceeding stiffness thereof while inserted in the body, and gives a feeling of physical disorder, which is the same defect as that of the tube having a tan $\delta_T$ of less than 0.5. On the other hand, those having a $G_T$ of less than 1 MPa can be squeezed by internal pressure due to a low mechanical strength. Since cannula, ED catheter, etc. are usually indwelled in the body for a long period, it is desirable to reduce the feeling of physical disorder to the least possible extent.

In the present invention, the aforementioned two physical properties were measured by the following ways.

tan $\delta_T$: Dynamic loss elastic modulus A and dynamic storage elastic modulus B were respectively measured, and A/B was calculated.

$G_T$: Using RMS800 an apparatus for measuring properties of polymer available from Rheometrics, Inc., Piscataway, N.J. as a measurement instrument, $G_T$ was measured under torsional vibration at 1.0 Hz frequency. The measurement of $G_T$,(A) and (B) can be obtained by using the RMS 800 by placing a sample in this machine and using standard measurements available with this machine.

The preferred medical tube is made of an organic polymer having a water absorption of not more than 5 wt %, preferably not more than 2 wt %, and particularly preferably not more than 1.5 wt %. When the water absorption exceeds 5 wt %, the swollen tube presses the surrounding tissue and gives a feeling of physical disorder. This is particularly evident when the medical tube of the present invention is used as a cannula, an ED catheter, or the like. The water absorption was measured at the body temperature of the animal to which the medical tube of the present invention was to be applied (e.g. at 36.5° C. for humans), in which a sample was immersed in water having a temperature corresponding to the body temperature for 24 hours, and the sample that absorbed water was dried at 150° C. for 30 minutes, and the separating water was measured by Karl Fischer's water measurement equipment.

From the viewpoint of penetration force, the medical tube of the present invention desirably has the above-mentioned flexibility after being inserted into the body, namely, at body temperature, and has a sufficient rigidity at room temperature before the insertion, or at a low temperature artificially prepared (e.g. 10–15° C.).

When the tube of the present invention is used as a cannula with a metal puncture needle (e.g. stainless puncture needle) as shown in FIG. 1, an insufficient rigidity just before the insertion into the body can cause a remarkable increase of the penetration force, since the tip of the cannula turns up apart from the puncture needle upon insertion, sometimes giving a sharp pain to patients. From this viewpoint, too, it is desirable that the cannula possess sufficient rigidity. Also, since ED catheters are intended for indwelling in duodenum through mouth or nose, throat, esophagus, and stomach, sufficient rigidity should be imparted to the catheter. Specifically, the catheter desirably has a $G_{T-10}/G_T$ of at least 2, preferably at least 3, and particularly preferably at least 8, wherein $G_{T-10}$ is a modulus of transverse elasticity at a temperature 10° C. lower than the body temperature.

The organic polymer to be used in the present invention may be made of any material as long as it is harmless to the target animals, and has a mechanical loss tangent of at least 0.5 at body temperature and a modulus of transverse elasticity of 1–1000 MPa at body temperature. Examples include polyurethane, styrene-butadiene copolymer and acrylonitrile-butadiene copolymer, with preference given to polyurethane.

The isocyanate component to be used for producing polyurethane is subject to no particular limitation and may be those normally used for polyurethanes, such as 2,4- or 2,6-tolylenediisocyanate, 4,4'-diphenylmethanediisocyanate, hexamethylenediisocyanate, m- or p-phenylenediisocyanate, isophoronediisocyanate, and so on which are used solely or in combination of one another. As the isocyanate component, 4,4'-diphenylmethanediisocyanate is particularly preferred.

As the polyol component, used are those having at least 2 active hydrogens, particularly hydroxyl groups, in one molecule, and polyoxyalkylenepolyol produced by the addition of alkylene oxide to a polyhydric alcohol such as diol and triol, an aliphatic amine, an aromatic amine, etc. as an initiator, polyesterpolyol produced by a condensation of an acid and an alcohol, polytetramethylene glycol, polybutadienepolyol, polypropylene glycol, poly(1,4-butane glycol adipate), poly(ethylene glycol adipate), polytetramethylene glycol, polyethylene glycol, and bisphenol A+propylene oxide, with particular preference given to bisphenol A+propylene oxide. The weight-average molecular weight of the polyols is preferably from about 200 to 2,000.

As the chain extender, used are glycols such as ethylene glycol, 1,4-butandiol and diethylene glycol, amines such as diethanolamine, triethanolamine, tolylenediamine and hexamethylenediamine, and polyisocyanates such as TDI (tolylenediisocyanate) adduct of trimethylolpropane, triphenylmethanetriisocyanate, bis(2-hydroxyethyl) hydroquinone, bisphenol A + ethylene oxide and bisphenol A+propylene oxide. Of those, particularly preferred is 1,4-butanediol.

The molar ratio of isocyanate component, chain extender, and polyol component is 1.5–3:0.5–2:1, and preferably 1.8–2.5:0.8–1.5:1. In the case of cannula and ED catheter only, the ratio is more preferably 1.9–2.2:0.9–1.2:1.

If necessary, a catalyst may be used for promoting the reaction. Examples of the catalyst are tertiary amines such as triethylamine, tetramethylhexamethylenediamine and tolylenediamine, and metal catalysts such as tin catalysts (e.g. stannous octylate, stannous oleate and dibutyl tin dilaurate) which are used solely or in combination.

Urethane is synthesized from an isocyanate, a polyol and a chain extender as mentioned above, with a catalyst optionally added as necessary. The method for the synthesis is disclosed, for example, in Japanese Unexamined Patent Publication No. 293214/1986 and Japanese Application No. 244341/1988 which corresponds to Japanese Unexamined Patent Publication No. 92914/1990 (US counterpart, U.S. patent application Ser .No. 413,771), now U.S. Pat. No. 5,145,935.

The medical tube of the present invention may be produced by a means known per se, such as extrusion molding, from the above-described materials.

The outer diameter of the medical tube of the present invention is, taking cannula for example, 0.5–2.8 mm, and preferably 0.6–2.3 mm, and the thickness thereof is 0.05–0.4 mm, and preferably 0.1–0.3 mm. In the case of ED catheter, the outer diameter is 1.0–4.0 mm, and preferably 1.6–3.5 mm, and the thickness is 0.1–1.2 mm, and preferably 0.2–0.7 mm.

The present invention is hereinbelow described in more detail by way of examples and comparative examples, to which the present invention is not limited.

EXAMPLES 1–10

COMPARATIVE EXAMPLES 1–5

Using various organic polymers for cannula, which are shown in Table 1, cannulae were produced by extrusion molding, and a puncture needle made of SUS304 (Japanese Industrial Standard, which corresponds to AISI304 of ASTM) was positioned therein. The chemical kind of the materials used and their physical properties measure at 26.5° C. and 36.5° C. are summarized in Table 1. Of the materials shown in Table 1, materials 1–10 were used for the cannulae of Examples 1–10, respectively, and materials 21–25 were used in Comparative Examples 1–5, respectively. The kinds and amounts (molar ratio) of isocyanate component, polyol component and chain extender used for the polyurethane shown in Table 1 are tabulated in Table 2.

TABLE 1

|  | Material No. | Chemical kind of material | Properties | | | | | |
|---|---|---|---|---|---|---|---|---|
|  |  |  | $\tan \delta_T$ $T = 36.5°$ C. | $\tan \delta_{T\_10}$ | $G_T$ (MPa) | $G_{T\_10}$ (MPa) | $G_{T\_10}/G_T$ | water absorption (wt %) at 36.5° C. |
| Example 1 | Material 1 | polyurethane | 2.0 | 0.4 | 30 | 500 | 16.7 | 1.5 |
| Example 2 | Material 2 | polyurethane | 1.2 | 0.2 | 20 | 400 | 20.0 | 1.5 |
| Example 3 | Material 3 | polyurethane | 0.5 | 0.06 | 20 | 50 | 2.5 | 1.5 |
| Example 4 | Material 4 | polyurethane | 1.5 | 0.3 | 80 | 700 | 8.8 | 1.5 |
| Example 5 | Material 5 | polyurethane | 1.2 | 0.2 | 180 | 1000 | 5.6 | 1.5 |
| Example 6 | Material 6 | polyurethane | 1.0 | 0.1 | 300 | 1000 | 3.3 | 1.5 |
| Example 7 | Material 7 | polyurethane | 0.5 | 0.06 | 500 | 1000 | 2.0 | 1.5 |
| Example 8 | Material 8 | polyurethane | 1.8 | 0.4 | 50 | 700 | 14.0 | 1.5 |
| Example 9 | Material 9 | polyurethane | 1.0 | 0.2 | 40 | 400 | 10.0 | 1.5 |
| Example 10 | Material 10 | polyurethane | 0.5 | 0.05 | 30 | 100 | 3.3 | 1.5 |
| Comp. Ex. 1 | Material 21 | polyurethane | 0.3 | 0.05 | 800 | 1000 | 1.3 | 1.5 |
| Comp. Ex. 2 | Material 22 | polyurethane | 0.1 | 0.05 | 1000 | 1000 | 1.0 | 1.5 |
| Comp. Ex. 3 | Material 23 | polyurethane | 0.2 | 0.05 | 30 | 50 | 1.7 | 1.5 |
| Comp. Ex. 4 | Material 24 | ETFE | 0.04 | 0.04 | 500 | 500 | 1.0 | 0.05 |
| Comp. Ex. 5 | Material 25 | polypropylene | 0.04 | 0.04 | 500 | 500 | 1.0 | 0.03 |

Note: ETFE = ethylene-tetrafluoroethylene copolymer, obtained from DU PONT-MITSUI FLUOROCHEMICALS CO., LTD.
polypropylene was obtained from MITSUI PETROCHEMICAL INDUSTRIES, LTD.

TABLE 2

| | Material and molar ratio | | | | | | | | | | | | |
|---|---|---|---|---|---|---|---|---|---|---|---|---|---|
| | Material No. | | | | | | | | | | | | |
| Component | 1 | 2 | 3 | 4 | 5 | 6 | 7 | 8 | 9 | 10 | 21 | 22 | 23 |
| diisocyanate component 4,4'-diphenylmethane-diisocyanate | 2.0 | 1.9 | 1.6 | 1.9 | 1.8 | 1.7 | 1.6 | 2.2 | 1.9 | 1.6 | 1.4 | 1.2 | 1.3 |
| polyol component | | | | | | | | | | | | | |
| bisphenol A + propylene oxide | 1.0 (1000) | 1.0 (1000) | 1.0 (1000) | 1.0 (900) | 1.0 (800) | 1.0 (700) | 1.0 (600) | | | | 1.0 (550) | 1.0 (450) | |
| polybutane glycol adipate | | | | | | | | 1.0 (450) | 1.0 (450) | 1.0 (450) | | | 1.0 (450) |
| chain extender 1,4-butane glycol | 1.0 | 0.9 | 0.6 | 0.9 | 0.8 | 0.7 | 0.6 | 1.2 | 0.9 | 0.6 | 0.4 | 0.2 | 0.3 |

Note: Figures in parentheses are weight-average molecular weights.

Experiment 1

The degree of the feeling of physical disorder caused by the tube of the present invention was examined.

FIG. 1 is a cross section of a cannula 1 used in the experiment. Cannulae containing an indwelling portion 4 having an outer diameter of 1.32 mm, an inner diameter of 0.96 mm, thickness of 0.18 mm, and length of 70 mm, which was made of the materials shown in Examples 1–10 and Comparative Examples 1–5, respectively, and a hub 2 made of polypropylene, held by plug 5 were produced by conventional extrusion molding using a core wire, within which a puncture needle 3 made of SUS304 having a sharpened tip was positioned. The indwelling portion had a tapered thin tip, and the thickness of the tip was about half that of the center portion.

Using each cannula produced as in the above, the degree of the feeling of physical disorder that each cannula gives to humans was examined, the results of which are summarized in Table 3.

Test Method

A cannula was inserted into each healthy subject (10 per group) from basilic vein in the left arm, and upon confirmation of the blood flow therethrough, only the puncture needle 3 was extracted. At three minutes after confirmation of the blood flow out from the hub side, the cannula was moved to examine the degree of the feeling of physical disorder.

Judgement Criteria

The physical disorder felt by each subject was expressed according to the following judgement criteria, and the average was taken as an index of the feeling of physical disorder of the ten subjects.

5 : physical disorder scarcely felt
4 : physical disorder somewhat felt
3 : physical disorder felt
2 : physical disorder felt rather strongly
1 : physical disorder felt strongly

Experiment 2

Each cannula used in Experiment 1 was examined for penetration force and turning up of the tip.

1. Evaluation of Turning Up

A cannula was punctured through six sheets of wrapping paper (white paraffin paper, medium size, 105 mm×105 mm) at a puncture speed of 100 mm/min., and turning up of the tip of the cannula was visually observed and compared with that of the cannulae of Comparative Examples. The results are summarized in Table 3.

2. Measurement of Penetration Force

Each cannula used in Experiment 1 was punctured through a natural rubber plate (1.5 mm thickness, Shore A hardness: 30) at a puncture speed of 100 mm/min., and penetration force (gf) of the straight section following the tip of the cannula was measured with tensile tester autograph Tensile Testor Autograph S500D available from Shimazu Corp., Japan, which was then compared with that of the cannulae of Comparative Examples. The results are summarized in Table 3.

TABLE 3

|  | Experiment 1 | Experiment 2 | |
|---|---|---|---|
|  | feeling of physical disorder | penetration force (gf) | turning up |
| Example 1 | 4.9 | 44.6 | none |
| Example 2 | 4.8 | 47.9 | none |
| Example 3 | 4.4 | 47.8 | none |
| Example 4 | 4.8 | 44.2 | none |
| Example 5 | 4.8 | 43.7 | none |
| Example 6 | 4.7 | 45.2 | none |
| Example 7 | 4.5 | 42.9 | none |
| Example 8 | 4.9 | 43.1 | none |
| Example 9 | 4.8 | 43.6 | none |
| Example 10 | 4.6 | 44.2 | none |
| Com. Ex. 1 | 3.8 | 43.1 | none |
| Com. Ex. 2 | 3.2 | 44.5 | none |
| Com. Ex. 3 | 3.8 | 44.9 | none |
| Com. Ex. 4 | 2.4 | 26.8 | none |
| Com. Ex. 5 | 2.2 | 69.5 | none |

EXAMPLES 11–12,

COMPARATIVE EXAMPLES 6–7

A tube made of materials described in Example 8 and having an outer diameter of 3.5 mm, an inner diameter of 3.0 mm, thickness of 0.25 mm, and length of 1200 mm (Example 11), and a tube made of materials described in Example 9 and having an outer diameter of 3.5 mm, an inner diameter of 3.0 mm, thickness of 0.25 mm, and length of 1200 mm (Example 12) were prepared by conventional extrusion molding (tube molding). On one end thereof, an inlet portion was formed, and a delivery portion was formed on the other end, and 0.5 g of a weight was set on the portion following the delivery portion to give an ED catheter. For comparison, ED catheters as described above containing tubes made of EVA (Comparative Example 6) and silicone (Comparative Example 7), respectively, both having an outer diameter of 3.5 mm, an inner diameter of 3.0 mm, thickness of 0.25 mm, and length of 1200 mm were prepared.

Experiment 3

The medical tube of the present invention was examined for easiness of insertion, pain after insertion, and the feeling of physical disorder.

Each ED catheter thus prepared was applied to six healthy humans from nose through throat, esophagus, and stomach to duodenum, and indwelled there for 24 hours, and easiness of insertion, and pain and the feeling of physical disorder during indwelling were examined, the results of which are summarized in Table 4.

TABLE 4

| | Example 11 | | Example 12 | | Comp. Ex. 6 | | Comp. Ex. 7 | |
|---|---|---|---|---|---|---|---|---|
| | insert-ability | feeling of physical disorder | insert-ability | feeling of physical disorder | insert-ability | feeling of physical disorder | insert-ability | feeling of physical disorder |
| Male (40) | fine | none | fine | none | fine | yes | poor | none |
| Male (55) | fine | none | fine | none | fine | yes | poor | none |
| Male (65) | fine | none | fine | none | fine | yes* | incapable | — |
| Female (40) | fine | none | fine | none | fine | yes* | poor | none |
| Female (55) | fine | none | fine | none | fine | yes* | incapable | — |
| Female (65) | fine | none | fine | none | fine | yes* | incapable | — |

Note: *accompanied by pain
Figures in parentheses are the age of the subjects.

The physical properties of EVA and silicone at 26.5° C. and 36.5° C., which were used in the Experiments of the present invention are as follows.

| | EVA | Silicone |
|---|---|---|
| $\tan \delta_T$ | $5 \times 10^{-2}$ | $3 \times 10^{-2}$ |
| $\tan \delta_{T-10}$ | $5 \times 10^{-2}$ | $3 \times 10^{-2}$ |
| $G_T$ | 22 MPa | 10.5 MPa |
| $G_{T-10}$ | 25 MPa | 10.5 MPa |
| $G_{T-10}/G_T$ | 1.1 | 1.0 |
| water absorption | 0.4 wt % | 0.1 wt % |

As is evident from the experimental results as described above, the medical tube of the present invention has excellent rigidity upon insertion into the body of animals, and can be easily inserted. While exhibiting sufficient squeeze resistance and buckling resistance during indwelling in the body, the tube of the present invention gives less feeling of physical disorder even with a long period of indwelling in the body, due to the flexibility greater than that of the conventional tubes.

In particular, a tube having a water absorption of not higher than 5 wt % does not swell in blood vessels, etc. as do the conventional highly hydrophilic tubes, and is advantageous in that it gives less feeling of physical disorder during use.

What is claimed is:

1. A medical tube for insertion into a mammal; said medical tube being made of a hydrophobic non-halogenated polyurethane which comprises an isocyanate component, a chain extender and a non-halogenated polyol component; said non-halogenated polyol component being a member selected from the group consisting of 1,4-butylene glycol adipate and a combination of bisphenol A and propylene oxide; said polyurethane having a water absorption at 36.5° C. of not more than 5 wt %, a mechanical loss tangent at 36.5° C. of at least 0.5, a modulus of transverse elasticity at 36.5° C. of 1–1000 MPa, and a modulus of transverse elasticity at a temperature of 26.5° C. that is at least twice said modulus of transverse elasticity at 36.5° C.

* * * * *